US011783933B2

(12) United States Patent
Gardner

(10) Patent No.: US 11,783,933 B2
(45) Date of Patent: Oct. 10, 2023

(54) DEVICE WITH IDENTIFIER

(71) Applicant: Smiths Medical ASD, Inc., Plymouth, MN (US)

(72) Inventor: Richurd Gardner, Boscawen, NH (US)

(73) Assignee: SMITHS MEDICAL ASD, INC., Plymouth, MN (US)

(*) Notice: Subject to any disclaimer, the term of this patent is extended or adjusted under 35 U.S.C. 154(b) by 1131 days.

(21) Appl. No.: 16/472,843

(22) PCT Filed: Feb. 2, 2018

(86) PCT No.: PCT/US2018/016633
§ 371 (c)(1),
(2) Date: Jun. 21, 2019

(87) PCT Pub. No.: WO2018/156336
PCT Pub. Date: Aug. 30, 2018

(65) Prior Publication Data
US 2019/0355463 A1     Nov. 21, 2019

Related U.S. Application Data

(60) Provisional application No. 62/462,448, filed on Feb. 23, 2017.

(51) Int. Cl.
*G16H 20/17*     (2018.01)
*G16H 10/60*     (2018.01)
(Continued)

(52) U.S. Cl.
CPC ............ *G16H 20/17* (2018.01); *A61M 5/315* (2013.01); *G16H 10/60* (2018.01); *G16H 40/63* (2018.01);
(Continued)

(58) Field of Classification Search
CPC ........ G16H 20/17; G16H 10/60; G16H 40/63; A61M 5/315; A61M 2205/3569; A61M 2205/6072; A61M 2205/60
See application file for complete search history.

(56) References Cited

U.S. PATENT DOCUMENTS 8,172,129 B1   5/2012   Laurenzi et al.
9,566,388 B1   2/2017   Jones
(Continued)

FOREIGN PATENT DOCUMENTS

| JP | 2005-152555 A | 6/2005 |
|---|---|---|
| WO | 99-47062 | 9/1999 |
| WO | 2008004670 A1 | 1/2008 |

OTHER PUBLICATIONS

PCT International Search Report and Opinion dated Jun. 26, 2018.

*Primary Examiner* — Matthew Mikels
(74) *Attorney, Agent, or Firm* — Louis Woo

(57) ABSTRACT

An identifier is provided to a medical device such as a syringe to uniquely identify the medical device. For a syringe, the unique identifier may be in the form of a bar code printed onto the thumb press, stem, or both at the plunger of the syringe. The bar code may be a 2-dimensional bar code or a 1-dimensional bar code. Alternatively, an RFID tag may be attached to the plunger, for example fitted to or embedded into the thumb press. The unique identifier provides, at minimum, the manufacturing data unique to the syringe so that the history of the syringe may be readily traced and associated with the medical records of the patient the syringe is used for.

17 Claims, 2 Drawing Sheets

(51) Int. Cl.
  *G16H 40/63* (2018.01)
  *A61M 5/315* (2006.01)
(52) U.S. Cl.
  CPC .............. *A61M 2205/3569* (2013.01); *A61M 2205/6072* (2013.01)

(56) References Cited

U.S. PATENT DOCUMENTS

| | | | |
|---|---|---|---|
| 2004/0186437 A1* | 9/2004 | Frenette | A61M 5/3129 604/189 |
| 2005/0148869 A1* | 7/2005 | Masuda | A61M 5/1456 600/432 |
| 2013/0204225 A1 | 8/2013 | Creaturo | |
| 2016/0001003 A1* | 1/2016 | Perazzo | A61M 5/1782 53/493 |

* cited by examiner

FIG. 1A
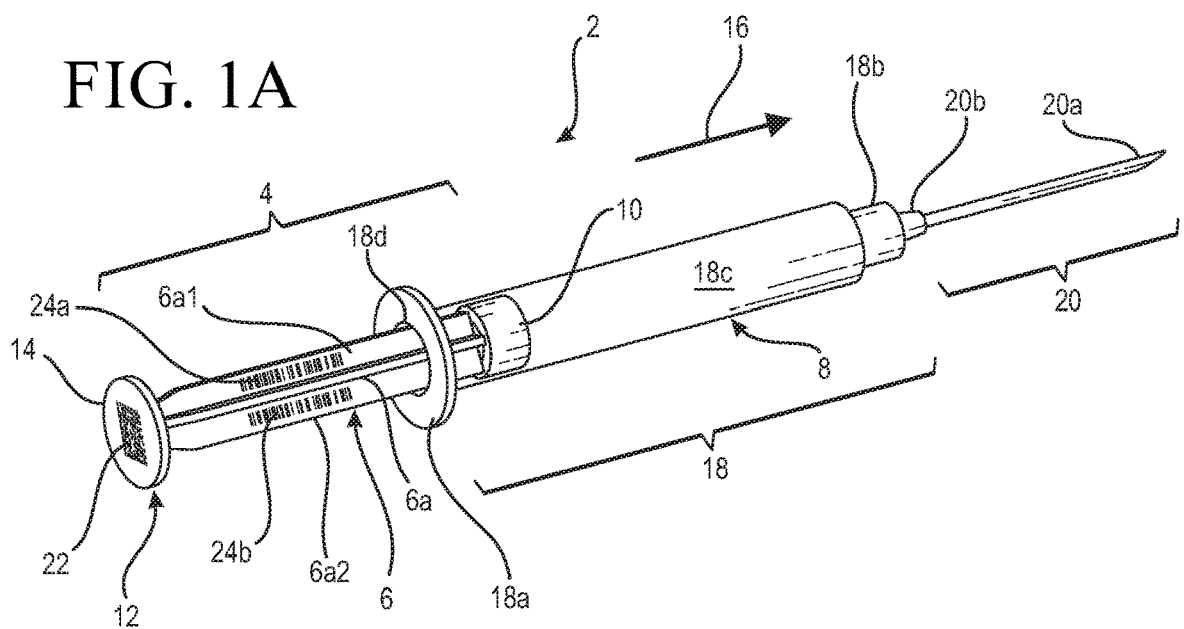
FIG. 1B
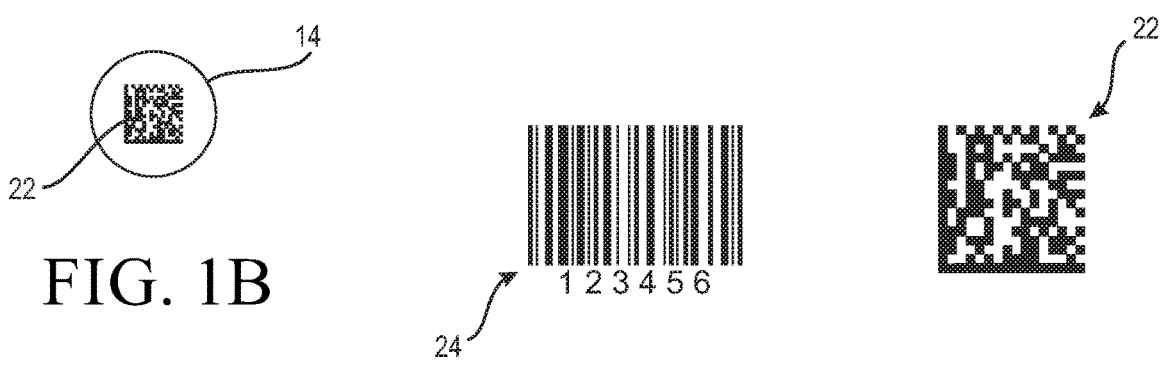
FIG. 2A  FIG. 2B
FIG. 4A
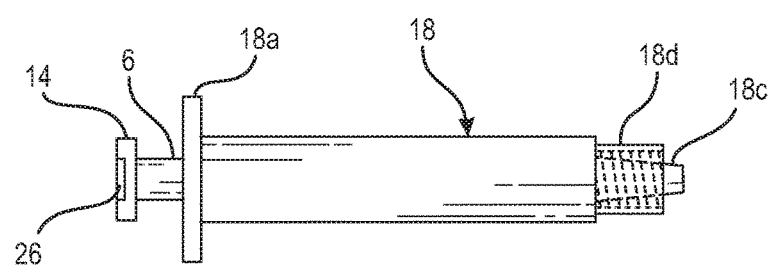
FIG. 4B
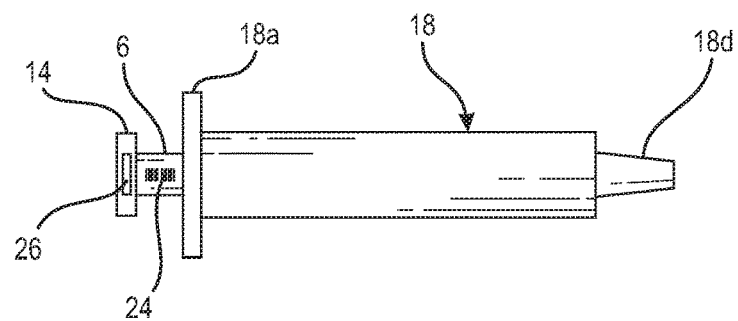

DEVICE WITH IDENTIFIER

FIELD OF THE INVENTION

The instant invention relates to devices with means for identifying those devices, and more particularly a medical device that has a unique identifier.

BACKGROUND OF THE INVENTION

In the medical field, for Class I devices that are implanted into a patient, identification means is attached to each of those devices to provide information about said each device. Such identification means may include a tag that provides data about the device and identifies the place of the device's manufacture as well as the device's manufacture date. Usually data relating to the device as set forth in the tag is recorded during the various stages the device is exposed starting from the time the device was manufactured to when the device is implanted into a patient, so that a record is established for the device that enables the tracing of the device all the way back to when it was manufactured.

Those medical devices that are not implanted into the patient, i.e., Class II devices, usually are manufactured in large quantities. The Class II devices that are manufactured at a given time period in a given facility usually are assigned a lot number so that all of those devices may be traced. However, oftentimes each of the lots produced may include hundreds, if not thousands and possibly millions, of the same devices, such as for example syringes, that may be manufactured over an extended period of time, for example a number of days. Consequently, if a defect is found in a particular one of the devices of the lot, it may be difficult to determine the particular time and the particular batch of material used to make the defective device. Pinpointing the time frame and the batch of material used to make the defective device is desirable because other devices made using the same manufacture process and machine(s) at substantially the same time frame with the same particular batch of material may then be recalled and examined. Otherwise, the whole lot of devices may have to be recalled.

Medical devices such as for example syringes often come in boxes that contain a plurality of the syringes. Each of those boxes may be a portion of a lot and are accordingly marked as such. Thus, were a box to contain 50 syringes, those syringes presumably are manufactured at the same time at the same facility. The syringes may be used to draw blood, and other blood gas procedures as is well known. There are also instances where medications are pre-stored in syringes for use in medical procedures. In addition, some diagnostic procedures for example X-ray (for angiography, venography, uroraphy), computer tomography (CT) scanning, magnetic resonance imaging (MRI), and ultrasound imaging require the injection of contrast media into the patients from syringes. Contrast media are also used for angioplasty and other radiographic therapeutic procedures. Thus, syringes manufactured from a given lot may be used in different procedures and accordingly may be used to store different fluids.

Most of the current syringes being used have transparent or translucent barrel bodies where graduation markings are printed to provide calibrated measurement of the amount of medication or fluid within the barrel body. To ensure that the syringe is associated with a particular patient, oftentimes a label is printed and attached to the barrel of the syringe, either before or after the procedure, so that the syringe and more particularly the fluid stored therein may be associated with the patient. Such association, however, only extends to the particular syringe, as it relates to the other syringes that were in the same box, or lot. The particular syringe cannot therefore be separately identified and traced other than that it is from a given box that belongs to a specific lot and was used for the particular patient.

There is therefore a need to provide a non-expensive yet unique identifier for each of the medical devices such as syringes that may be mass produced in large quantities so that each of the devices may be individually traced from the time it was manufactured to its disposal.

BRIEF SUMMARY OF THE INVENTION

The instant invention provides a device with a unique identifier that allows the device, for example a medical device such as a syringe, to be traced from its origin to its use and final disposition. The identifier may be in the form of a bar code or an electronic identification means such as a radio-frequency identification (RFID) tag. In the case of a syringe, the unique identifier is provided to the plunger of the syringe to ensure that the unique identifier remains on the syringe from its manufacture date until its use and disposal. With regard to the plunger, the unique identifier, in the case of a bar code, may be printed onto the thumb press or press plate of the plunger. Such bar code may be a 2-dimensional (2-D) bar code that contains a large amount of information when scanned. The information may include, at minimum, the date of manufacture, place of manufacture and possibly the materials used. Other pertinent data relating to the particular device for example the size of the lot may also be stored in the bar code. Instead of the press plate, a 1-dimensional (1-D) bar code may be printed onto the stem of the plunger. Were the stem a rib type stem, the 1-D bar code may be printed onto one or several of the ribs of the stem. In the case where the stem is cylindrical, only one bar code is needed. In place of a bar code, an RFID or other similar electronic store tag may be embedded or attached to the plunger, with the press plate being the most efficient place to provide the tag for the plunger.

With a unique identifier for each given syringe, were the given syringe used for a specific procedure with a particular patient, when the unique identifier is scanned, read or entered into the presumably electronic medical file record of the particular patient either before or after the specific procedure, the data relating to the given syringe is recorded and associated with the specific procedure for the particular patient. The detailed history of the given syringe is therefore added to the updated medical history of the patient. Thus, assuming the given syringe is disposed of after the specific procedure, the medical record of the particular patient, in addition to containing the medical history of the patient, would also contain a complete history of the given syringe.

The present invention therefore relates to a syringe comprising a barrel body having a connector end and an open end, a plunger including a stem having a piston at one end slidably fitted within the barrel body and a press plate at other end to enable a user to move the plunger relative to the barrel body, and an indicia provided to the plunger to convey information relating to the syringe.

The present invention also relates to a device having an elongate cylindrical tube including a connector end and an open end, a plunger including a stem having a piston at one end slidably fitted within the tube and a press plate at other end to enable a user to move the plunger relative to the tube, wherein the plunger has a unique identifier having stored therein information relating to the device.

The present invention yet also relates to a method of making an information bearing device, comprising:

providing an elongate cylindrical tube having a connector end and an open end;

providing a plunger including a stem having a piston at one end and a press plate at other end;

assembling the piston into the tube body through the open end so that the piston is slidable along the tube by moving the plunger; and providing an indicia containing information relating to the device to the plunger.

BRIEF DESCRIPTION OF THE FIGURES

The present invention will become apparent and the invention itself will be best understood with reference to the following description of the invention taken in conjunction with the accompanying drawings, wherein:

FIG. 1A is a perspective view of a syringe of the instant invention;

FIG. 1B is an end view of the press plate of the syringe of FIG. 1A;

FIG. 2A is an exemplar 1-dimensional bar code;

FIG. 2B is an exemplar 2-dimensional bar code;

FIG. 4A is an illustration of a luer lock type syringe with a unique identifier provided to its plunger; and FIG. 4B is a slip type syringe having a unique identifier embedded in the press plate of its plunger.

DETAILED DESCRIPTION OF THE INVENTION

Figure 3:
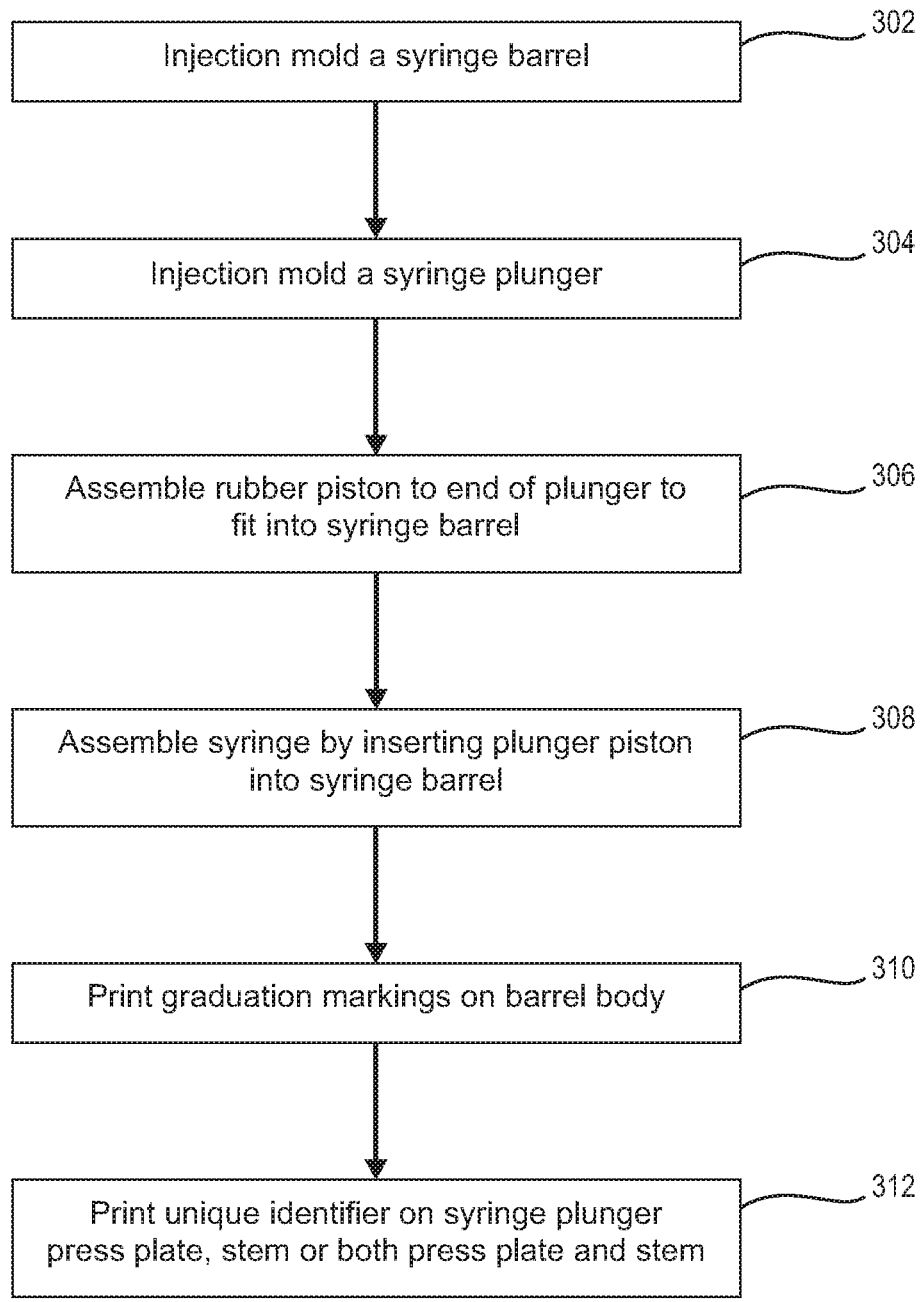
FIG. 3 is a flow chart illustrating the process of making the inventive medical device.

FIG. 1A shows an exemplar medical device in the form of a syringe 2 having a plunger 4 that has a stem or handle 6 with a distal end 8 having attached thereto an elastomeric or rubber piston 10. Stem 6, as shown in the exemplar syringe of FIG. 1A, is of the rib type in which a plurality of ribs 6a, for example four, extend longitudinally from distal end 8 to a proximal end 12. Integrally formed at proximal end 12 is a thumb press or press plate 14 whereon a user or clinician can place her thumb to push or move the plunger in the direction as indicated by directional arrow 16.

Syringe 2 also includes an elongate cylindrical tube that is conventionally referred to as the barrel or body 18 of the syringe. As shown, barrel 18 has a flange 18a at its proximal end and at its distal end a connector, possibly in the form of a conventional luer connector or the CorrectInject® (CI) type connector specific to some of the medical devices from the assignee of the instant application. As is well known, barrel 18 is an elongate tube whereinto its interior elongate cavity 18c a medication or other fluids may be stored for injection to a patient. Alternatively, cavity 18c of barrel 18 may be used to store blood drawn from a patient for well known medical procedures including for example blood lab tests or blood gas analysis. Although not shown in FIG. 1A, it is well known that graduation markings indicating the volume of fluid stored in cavity 18c may be provided, by a conventional printing process for medical plastics for example, onto the body of the syringe barrel 18.

With further reference to FIG. 1A, attached to connector 18b of barrel 18 is a needle assembly 20 that includes a needle 20a extending from a needle hub 20b. As is well known, needle hub 20b is matingly coupled to a tapered conical extension such as for example conical extensions 18c and 18d at the distal end of the respective syringes shown in FIGS. 4A and 4B. Syringe barrel 18 and plunger 6 each may be formed by a conventional injection molding process using a medical polymeric material, such as for example polyethylene, polyethylene-terephthalate (PET), cyclic olfien polymer, polystyrene, polyvinylidene chloride, polyethylene napthalate (PEN) or nylon, depending on the potential use for the syringe.

After the respective injection moldings of the syringe barrel 18 and the syringe plunger 4, the syringe is assembled by the insertion of the plunger, more in particular the distal end 8 of the plunger, into the open end 18d at the flange 18a at the proximal end of the syringe barrel 18, as is done conventionally. There is a tight slidable fit between the interior of the barrel body of the syringe, i.e., between the inner circumferential wall of the elongate tube as designated by cavity 18c and the outer circumferential wall of the rubber piston 10, so that a vacuum may be effected within cavity 18c for withdrawing blood from the patient when the plunger is moved in a direction opposite to that as indicated by directional arrow 16. The withdrawn blood stored in the syringe barrel body may then be used for tests, for example a blood gas analysis of the patient as discussed above. With the piston being slidably fitted within syringe barrel 18, the fluid stored in cavity 18c may be expelled from syringe barrel 18 by the clinician pressing her thumb against press plate 14 while holding flange 18a with two fingers so as to move plunger 4 in the direction as indicated by directional arrow 16.

To ensure that each individual syringe can be traced from its manufacturing to its final use, for the inventive syringe medical device, a readable or scannable indicia representative of a unique identifier is provided to the syringe plunger 4. For the syringe of the instant invention, at the time of manufacture, a unique identifier, in the form of a 2-D bar code 22 such as the example the 2-D bar code 24 shown in FIG. 2B, may be permanently printed onto the surface of press plate 14 by way of a conventional process for printing readable indicia onto a plastic surface such as for example the printing of the graduate markings onto the syringe barrel body as discussed above. The 2-D bar code indicia printed onto the press plate 14 is impervious to fluid and does not come off easily and thus remains with the syringe from the time it is printed thereon to the disposal of the syringe. A particular bar code number may be assigned to each of the syringes, so that the bar code printed onto the plunger of each syringe is unique to said each syringe. As should be appreciated, a substantial amount of information may be stored in a 2-D bar code, so that the manufacturing data of the syringe which may include its site of manufacture, the date of manufacture, the type of material it is made from as well as other features of interest, may be stored in the bar code.

As an alternative to the 2-D bar code, or in conjunction therewith, a 1-D bar code such as the exemplar 1-D bar code 24 shown in FIG. 2A may be printed onto one or more ribs 6a of the syringe plunger 4. For the exemplar syringe shown in FIG. 1A, a 1-D bar code 24a is printed onto rib 6a1 of stem 6. Although one 1-D bar code printed on a given rib of the plunger stem is deemed sufficient, to enhance efficiency and readability, the 1-D bar code may be printed onto more than one, or all, of the ribs of the plunger stem. This is illustrated by the additional 1-D bar code 24b printed onto rib 6a2 of stem 6 of the syringe in FIG. 1A. In the case that the stem of the plunger is an elongate cylindrical stem, only one 1-D bar code is needed to be printed onto the cylindrical stem. Although the 1-D bar code is adapted to store less data than a 2-D bar code, it nonetheless is sufficient to store all of the pertinent information required to uniquely identify the syringe, i.e., from its origin data to its final usage data.

With a unique identifier in the form of a readable or scannable indicia such as a bar code associated with each manufactured syringe, when the syringe is used, the clinician only needs to scan or read the indicia bar code and enter the patient procedure that the syringe is to be used with, as well as the patient data, into a medical records computer system that may be used with the scanner or reader. That way, the information relating to the particular syringe is associated with the medical records of the patient that is presumably stored in the electronic medical file history of the patient in the computer system. Given that bar code scanners (or reader) and computer system that includes storage servers that operate with the scanners to store patient files are well known, no further discussion of the scanners and possible computer systems that may be used with the scanners is deemed necessary.

With a readable unique identifier marked thereon, when a medical device is used for a given procedure for a patient, the history of the medical device as well as the procedures performed on the patient with the medical device could be readily traced. For the exemplar medical device syringe, the unique identifier allows a record be made of the association of the syringe with the patient and the procedure that the syringe was used for (for example withdrawing blood for blood gas analysis or for simple blood tests, or injecting a given medicament, contrast medium or fluid into the patient). The amount of medicament or fluid input to the patient or the amount of blood withdrawn from the patient are also recorded onto the medical records of the patient for association with the syringe. In addition to a syringe, the unique identifier may be printed onto any other Class II medical device were there a need to trace that medical device from its manufacture to its use and subsequent disposal.

The process of making the uniquely identifiable syringe is illustrated in the flow chart of FIG. 3. Using the conventional injection molding process, the syringe barrel is injection molded in step 302, and the syringe plunger is injection molded in step 304. Of course, instead of injection molding, other types of conventional plastic molding techniques such as blow molding and compression molding may also be used to make the syringe barrel and the syringe plunger. Further, the injection molding of the syringe barrel and plunger may be done at the same time from different assembly lines as is well know. In any event, after the forming of the syringe barrel and the syringe plunger, the elastomeric or rubber piston is assembled to the end of the plunger that fits into the syringe barrel, per step 306. Thereafter, the syringe is assembled by the insertion of the plunger piston, as well as a portion of the plunger stem, into the syringe barrel, as per step 308. In most instances, graduation markings are printed onto the syringe barrel body, as per step 310. At the same time or thereafter, or for that matter, before the plunger end with the piston is fitted into the syringe, a unique identifier is provided to the syringe plunger for example by printing, either at its press plate, at the stem, or at both the stem and the press plate, as per shown in step 312.

Although it is envisioned that a 2-D bar code printed onto the press plate is sufficient, there may be instances where 1-D bar code(s) may also be printed onto the stem to facilitate the scanning of the bar code. Alternatively, instead of printing a 2-D bar code onto the surface of the press plate, the printing of a 1-D bar code(s) to the stem of the plunger may be desirable. Furthermore, it may enhance the scanning of the bar code indicia by having bar codes printed onto both the press plate as well as the stem of the plunger. Thus, it should be appreciated that the exemplar inventive syringe as per shown in FIG. 1A shows both the 2-D bar code at the press plate and the 1-D bar code(s) at the ribs of the stem.

In practice, a syringe of the instant invention may contain only one bar code, either printed on the press plate or the stem of the plunger. Furthermore, even though it is discussed above that a 2-D bar code is printed onto the press plate and a 1-D bar code printed onto the rib of the stem, it should be appreciated that a 1-D bar code may also be printed onto the press plate while a 2-D bar code (with sufficiently small but scannable or readable dimension) may be printed onto the plunger. In other words, as long as a unique identifier is provided to the plunger so that the syringe has the unique identifier from its origin to its disposal, the recording of the history as well as the tracing of the syringe can be effected.

An alternative of the instant invention can be gleaned from FIGS. 4A and 4B. For ease of discussion, the same reference numbers used to designate the FIG. 1 syringe are used to designate similar components for the syringes of FIGS. 4A and 4B. As shown, FIG. 4A illustrates a syringe having a locking type connector end 18b in the manner similar to that of the syringe as shown in FIG. 1A. Connecter 18b has an internal thread (shown by the dotted line) adapted to threadingly mate with a flange of a needle assembly such as 20 shown in FIG. 1A. The component 18c of FIG. 4A is a male portion of the connector adapted to accept the needle hub 20b of the needle assembly 20 as shown in FIG. 1A. Structurally, the syringe shown in FIG. 4A is substantially the same as the syringe shown in FIG. 1A. The one difference is that the stem or handle 6 of the syringe shown in FIG. 4A is cylindrical, instead of being ribbed.

For the syringe of FIG. 4A as well as that of FIG. 4B, instead of a bar code printed onto the press plate, a unique identifier in the form of a radio frequency identification (RFID) tag 26 is fitted into a cavity formed at press plate 14. As is well known, an RFID tag uses electromagnetic fields to automatically identify the devices it is attached to, in this case the syringe. With the inventive syringe, chances are the RFID tag is a passive tag that would collect the energy of the interrogation radio waves from a nearby RFID reader so that information stored in the RFID tag may be conveyed to the reader. Thus, same as in the bar code, information that is unique to the syringe may be stored in the RFID tag and may be used in the same manner as the information stored in the bar code as discussed above.

FIG. 4B shows a syringe that has a slip fit connector designated 18d to which the needle hub 20b of the needle assembly 20 may be fitted. The rest of the syringe as shown in FIG. 4B is the same as that shown in FIG. 4A. However, instead of having the RFID tag fitted into the cavity formed at the surface of the press plate 14, the tag 26 may be embedded into the press plate 14 so as not to be exposed. The same with the syringe of FIG. 4A, the information stored in the RFID tag 26 may be read by an RFID reader, as is conventionally known.

It should be appreciated that the present invention is subject to many variations, modifications and changes in detail. For example, instead of being attached to the press plate, the RFID tag may be embedded into the stem of the plunger. Further, instead of the plunger, a portion of the syringe barrel away from the graduate markings may first be printed with a non-clear background such as white. A bar code may then be printed onto the non-clear background. Therefore, it is intended that this invention be limited only by the scope of the herein appended claims.

The invention claimed is:

1. A device having an elongate cylindrical tube including a connector end and an open end, a plunger including a stem having a piston at one end slidably fitted within the tube and a press plate at other end to enable a user to move the plunger relative to the tube, wherein a unique identifier is permanently provided to the plunger of the device at the time of manufacture of the device to store manufacture data of the device, the unique identifier adapted to be read or scanned and associated with patient data relating to at least the procedure and amount and type of medicament the device is used for a patient in a data record file stored in a memory of a computer system such that the device can be individually traced and the history of the device is accessible from its manufacture to its disposal.

2. The device of claim 1, wherein the manufacture data of the device stored in the unique identifier includes date and site of manufacture of the device; and
wherein the data record file of the unique identifier is associated with the medical records of the patient that the device is used with.

3. The device of claim 1, wherein the unique identifier comprises a 2-dimensional bar code printed onto or embedded into the press plate of the plunger.

4. The device of claim 1, wherein the unique identifier comprises a 1-dimensional bar code printed onto the stem of the plunger.

5. The device of claim 1, wherein the unique identifier comprises an electronic tag provided to the press plate or the stem of the plunger.

6. The device of claim 1, wherein the unique identifier comprises an electronic tag or a bar code attached to the plunger.

7. The device of claim 1, wherein the device comprises a syringe.

8. A method of making an information bearing device, comprising:
providing an elongate cylindrical tube having a connector end and an open end;
providing a plunger including a stem having a piston at one end and a press plate at other end;
assembling the piston into the tube body through the open end so that the piston is slidable along the tube by moving the plunger; and
permanently providing an identifier uniquely associated with said device that contains manufacture data of said device to the plunger;
enabling the identifier to be read or scanned and be associated with patient data relating to at least the procedure and the amount and type of medicament the device is used for a patient in a data record file stored in a memory of a computer system such that the device can be individually traced and the history of the device is accessible from its manufacture to its disposal.

9. The method of claim 8, wherein the identifier is a 2-dimensional bar code, the method comprising:
printing the 2-dimensional bar code onto the press plate of the plunger.

10. The method of claim 8, wherein the identifier is a 1-dimensional bar code, the method comprising:
printing the 1-dimensional bar code onto the stem of the plunger.

11. The method of claim 8, wherein the identifier comprises a 2-dimensional bar code and a 1-dimensional bar code, the method comprising:
printing the 2-dimensional bar code onto the thumb plate of the plunger and the 1-dimensional bar code onto the stem of the plunger.

12. The method of claim 8, wherein the identifier is an electronic tag, the method comprising:
embedding the tag to the press plate of the plunger.

13. The method of claim 8, wherein the identifier is a bar code or an electronic tag, the method comprising:
attaching the bar code or electronic tag to the plunger.

14. The method of claim 8, comprising the steps of:
including in the identifier the date and site of manufacture of the device; and
storing information associated with the patient that the device is used for as part of the data record file.

15. The device of claim 1, wherein the unique identifier comprises an electronic tag embedded into the press plate of the plunger.

16. The method of claim 8, wherein the identifier is an electronic tag, the method comprising:
embedding the tag to the press plate of the plunger.

17. The device of claim 3, further comprising another identifier printed onto at least one of the ribs of the stem of the plunger.

* * * * *